US010170846B2

(12) United States Patent
Hilz et al.

(10) Patent No.: US 10,170,846 B2
(45) Date of Patent: Jan. 1, 2019

(54) ELECTRODE AND CABLE CONNECTIONS IN ELECTROCARDIOGRAPHY SYSTEMS (71) Applicant: Heart Test Laboratories, Inc., Westlake, TX (US)

(72) Inventors: Mark Hilz, Argyle, TX (US); Paul Klotz, Canyon, TX (US); Mark Tiegs, West Allis, WI (US)

(73) Assignee: Heart Test Laboratories, Inc., Southlake, TX (US)

( * ) Notice: Subject to any disclaimer, the term of this patent is extended or adjusted under 35 U.S.C. 154(b) by 0 days.

(21) Appl. No.: 15/454,821

(22) Filed: Mar. 9, 2017

(65) Prior Publication Data
US 2017/0258355 A1 Sep. 14, 2017

Related U.S. Application Data (60) Provisional application No. 62/305,958, filed on Mar. 9, 2016.

(51) Int. Cl.
H01R 4/48 (2006.01)
A61B 5/0408 (2006.01)
A61B 5/00 (2006.01)
H01R 11/22 (2006.01)
A61B 5/0416 (2006.01)

(52) U.S. Cl.
CPC ............. H01R 4/48 (2013.01); A61B 5/0408 (2013.01); A61B 5/04085 (2013.01); A61B 5/6833 (2013.01); H01R 11/22 (2013.01); A61B 5/0416 (2013.01); A61B 2562/222 (2013.01); A61B 2562/226 (2013.01); A61B 2562/227 (2013.01); H01R 2201/12 (2013.01)

(58) Field of Classification Search
CPC ...... H01R 11/22; H01R 2201/12; H01R 4/48; A61B 2562/225; A61B 5/04085; A61B 5/0416
USPC ....... 439/726, 729, 789, 801, 803, 806, 835, 439/856, 909
See application file for complete search history.

(56) References Cited

U.S. PATENT DOCUMENTS 3,901,218 A 8/1975 Buchalter
4,220,387 A 9/1980 Biche et al.
(Continued)

FOREIGN PATENT DOCUMENTS

WO WO-2016034466 A1 3/2016

OTHER PUBLICATIONS

"International Application Serial No. PCT/US2017/021632, International Search Report dated Oct. 11, 2017", 7 pgs.
(Continued)

Primary Examiner — Eunhwa Kim
(74) Attorney, Agent, or Firm — Schwegman Lundberg & Woessner, P.A.

(57) ABSTRACT

In electrocardiography (ECG) system, a patient cable connecting one or more electrodes to a processing device for processing ECG signals may include one or more electrode connectors mechanically keyed to respective electrodes and/or a device connector mechanically and/or electronically keyed to a cable connector of the processing device. In some embodiments, keying between the cable and electrode is achieved, for example, with an electrode including a hollow-post portion that defines a bore in conjunction with a post protruding from an arm of the electrode connector that is sized to fit within the bore.

10 Claims, 6 Drawing Sheets

(56) References Cited

U.S. PATENT DOCUMENTS

| | | | | |
|---|---|---|---|---|
| 4,550,961 | A | * | 11/1985 | Aicher ................ H01R 13/627 439/348 |
| 4,674,015 | A | | 6/1987 | Smith |
| 4,797,125 | A | * | 1/1989 | Malana ................ A61B 5/0416 439/729 |
| 5,261,402 | A | | 11/1993 | Disabito |
| 5,380,222 | A | | 1/1995 | Kobayashi |
| 5,700,160 | A | | 12/1997 | Lee |
| 5,743,754 | A | | 4/1998 | Christich |
| 6,024,607 | A | | 2/2000 | Wahl |
| 6,062,915 | A | * | 5/2000 | Costello ................ H01R 11/24 439/729 |
| 6,223,088 | B1 | * | 4/2001 | Scharnberg ............ A61N 1/046 439/909 |
| 6,582,251 | B1 | | 6/2003 | Burke et al. |
| 6,854,994 | B2 | | 2/2005 | Stein et al. |
| 7,255,609 | B1 | | 8/2007 | Epstein |
| 9,226,680 | B1 | * | 1/2016 | Kendricks ............ A61B 5/0416 |
| 2008/0085615 | A1 | | 4/2008 | Xie et al. |
| 2008/0214064 | A1 | | 9/2008 | Pereira et al. |
| 2009/0099423 | A1 | | 4/2009 | Al-Ali et al. |
| 2010/0168547 | A1 | | 7/2010 | Kendricks |
| 2011/0017491 | A1 | | 1/2011 | Lu et al. |
| 2013/0078869 | A1 | | 3/2013 | Golko et al. |
| 2014/0213112 | A1 | | 7/2014 | Bandis et al. |
| 2015/0093184 | A1 | | 4/2015 | Henry |
| 2015/0349569 | A1 | | 12/2015 | Christensen et al. |
| 2016/0081534 | A1 | | 3/2016 | Lisogurski et al. |

OTHER PUBLICATIONS

"International Application Serial No. PCT/US2017/021632, Written Opinion dated Oct. 11, 2017", 16 pgs.

"International Application Serial No. PCT/US2017/021632, Invitation to Pay Add'l Fees and Partial Search Rpt dated Jun. 30, 2017", 15 pgs.

"Dsub Series", [Online]. Retrieved from the Internet: <URL:http://www.jae.com/jccom/en/connectors/detail/Dsub, (accessed Oct. 11, 2016), 1-2.

"Secure Keyed Mtp® Solutions", [Online]. Retrieved from the Internet: <URL:http://www.usconec.com/products/connectors/mtp_keyed_connectors.htm>, (accessed Oct. 11, 2016), 1-2.

* cited by examiner

ELECTRODE AND CABLE CONNECTIONS IN ELECTROCARDIOGRAPHY SYSTEMS

CROSS-REFERENCE TO RELATED APPLICATION

This application claims priority to and the benefit of, and incorporates herein by reference in its entirety, U.S. Provisional Patent Application No. 62/305,958, filed on Mar. 9, 2016.

TECHNICAL FIELD

The present disclosure relates to electrode assemblies and cables for connecting electrodes to a processing device, as used, for example, in electrocardiography systems.

BACKGROUND

Electrocardiography systems serve to monitor the electrical activity of the heart by recording and processing electrical signals measured with a number of electrodes placed on a patient's body. An electrocardiography system generally includes, in addition to the (one or more) electrodes, a processing device (e.g., a general-purpose computer running suitable software) connected to the electrodes via a suitable cable.

In conventional electrocardiography systems, the electrical signals for a number of leads (that is, electrodes or combinations thereof) are displayed on-screen or printed, in the form of time-varying waveforms called electrocardiograms, for interpretation by a clinician. The electrocardiograms usually exhibit a periodicity corresponding to the patient's heart beat and, within the signal portion for each cardiac cycle, characteristic features (such as peaks, decays, waves, etc., including, e.g., the QRS complex and T wave) corresponding to various physiological processes, such as depolarization and repolarization of the ventricles of the heart. More recently developed advanced electrocardiography systems moreover process the electrocardiograms, using new signal-processing techniques and algorithms, to obtain, e.g., time-frequency maps of the electrical activity or quantitative metrics of heart condition and health that increase the diagnostic potential of electrocardiography.

Most conventional electrocardiography systems measure signals in the millivolt range, as the entire amplitude of a QRS complex can be seen on a +/−5 mV scale (and most systems display the signals on a +/−2 mV scale). Signals less than 0.1 mV are typically considered noise, and are undesirable for final electrocardiogram readings. In fact, most electrocardiography systems implement filtering to hide stand-alone signals of low voltages. As a result, accuracy in the lower voltages (corresponding to the least significant bits) of an acquired signal have not been an important design goal of these systems, and often cost considerations drive design decisions to adopt less accurate materials for the electrodes and cables. For most of these systems, that is a reasonable trade-off. The above-mentioned advanced electrocardiography systems, however, involve signal-processing techniques that are contingent upon a higher information content and accuracy of the incoming electrical signals, with noise levels as low as a few microvolts. Using conventional, off-the-shelf electrodes and cables in these systems can degrade the accuracy and performance of the advanced signal-processing techniques.

SUMMARY

Electrocardiography systems in accordance with various embodiments employ high-quality, high-sensitivity electrodes and cables to meet the high-accuracy, low-noise requirements of advanced electrocardiogram-signal-processing techniques. Further, to limit connectability of processing devices implementing the advanced signal-processing functionality to only those types of cables and electrodes that meet the signal-quality requirements and thereby ensure proper operation of the electrocardiography system, the cables are keyed to both the electrodes and the processing devices.

In one aspect, the disclosed subject matter pertains to an electric cable that includes one or more electrode connectors at a first end of the cable. At least one of the electrode connectors includes a pair of clamp arms connected at least at an axis and rotatable relative to each other about the axis (herein also the "axis of rotation"). A first one of the clamp arms includes a post protruding from the clamp arm parallel to the axis of rotation. A second one of the clamp arms includes, at an inner surface thereof opposite to the post, an electrically conductive contact surface (herein also "inner contact surface"). The contact surface is electrically connected to a wire running within the cable. The clamp arms may be configured to engage with a hollow-post electrode: the post may, for instance, be sized to fit within a bore of the hollow-post electrode, and the contact surface may be complementary in shape to a portion of an exterior surface of the hollow-post electrode. The clamp arms, at least portions of which may be made of medical-grade plastic, may be operable to open at a clamp end of the clamp arms upon application of pressure onto grabber ends of the clamp arms and to close at the clamp end upon release of the pressure. The cable may further include a device connector at a second end of the cable. The device connector may include a plug having a pair of parallel edges of differing lengths and, protruding from the plug, a plurality of contacts enclosed by a trapezoid shroud with a pair of parallel edges, a shorter one of the pair of parallel edges of the trapezoid shroud being adjacent a longer one of the pair of parallel edges of the plug and a longer one of the pair of parallel edges of the trapezoid shroud being adjacent a shorter one of the pair of parallel edges of the plug. The device connector may be mechanically and/or electronically keyed to a mating cable connector of a processing device.

In another aspect, the disclosed subject matter provides an electrode assembly including an adhesive-tape backing; an electrode extending through an opening in the adhesive-tape backing; and a hydrogel patch. The electrode includes a ring-shaped disk portion adhering to a first side of the adhesive-tape backing and a hollow-post portion protruding from the second side of the adhesive-tape backing, and the hydrogel patch is disposed on the first side of the adhesive tape over the ring-shaped disk portion of the electrode.

In a further aspect, the disclosed subject matter relates to a system including one or more electrodes and a cable including one or more respective electrode connectors configured to engage with the one or more electrodes. Each of the electrodes includes a hollow-post portion defining a bore. Each electrode connector includes a pair of clamp arms connected at, and rotatable relative to each other about, an axis of rotation. A first one of the clamp arms includes a post sized and shaped to fit within the bore of the hollow-post portion of the respective electrode, and a second one of the clamp arms has an electrically conductive inner contact surface complementary in shape to a portion of an exterior surface of the hollow-post portion. The inner contact surface is electrically connected to a wire running within the cable. The post may protrude from the clamp arm parallel to the axis of rotation, and the inner contact surface may be positioned opposite to the post. The one or more electrodes may form part of one or more respective electrode assemblies, each electrode assembly further including a backing through which the electrode extends and a hydrogel patch disposed on the backing on a side opposite the hollow-post portion.

The system may further include a processing device configured to process signals acquired by the one or more electrodes, and the cable may include, at an end opposite the one or more electrode connectors, a device connector configured to mate with a cable connector of the processing device. In some embodiments, the device connector is mechanically keyed to the cable connector. For example, the device connector may include a plug configured to be received within a jack of the cable connector and having a pair of parallel edges of differing lengths, and, protruding from the plug, a plurality of contacts enclosed by a trapezoid shroud with a pair of parallel edges, a shorter one of the pair of parallel edges of the trapezoid shroud being adjacent a longer one of the pair of parallel edges of the housing and a longer one of the pair of parallel edges of the trapezoid shroud being adjacent a shorter one of the pair of parallel edges of the housing. Alternatively or additionally to being mechanically keyed to the cable connector, the device connector may be electronically keyed to the cable connector via a non-standard pin assignment.

In yet another aspect, the disclosed subject matter pertains to a method for connecting a hollow-post electrode to a processing device. The method involves use of a cable having, on one end of the cable, an electrode connector with a pair of hinged clamp arms and, on the other end of the cable, a device-connector. The method includes connecting the electrode connector to the hollow-post electrode by opening the hinged clamp arms, inserting a post extending from one of the arms into a mating bore in the hollow-post electrode, and closing the clamp arms to bring an inner contact surface of the other one of the clamp arms into contact with an exterior surface of the hollow-post electrode; and inserting the device-connector into a mating cable connector within the processing device.

BRIEF DESCRIPTION OF THE DRAWINGS

The foregoing will be more readily understood from the following detailed description, in particular, when taken in conjunction with the accompanying drawings, in which.

DETAILED DESCRIPTION

Figure 1:
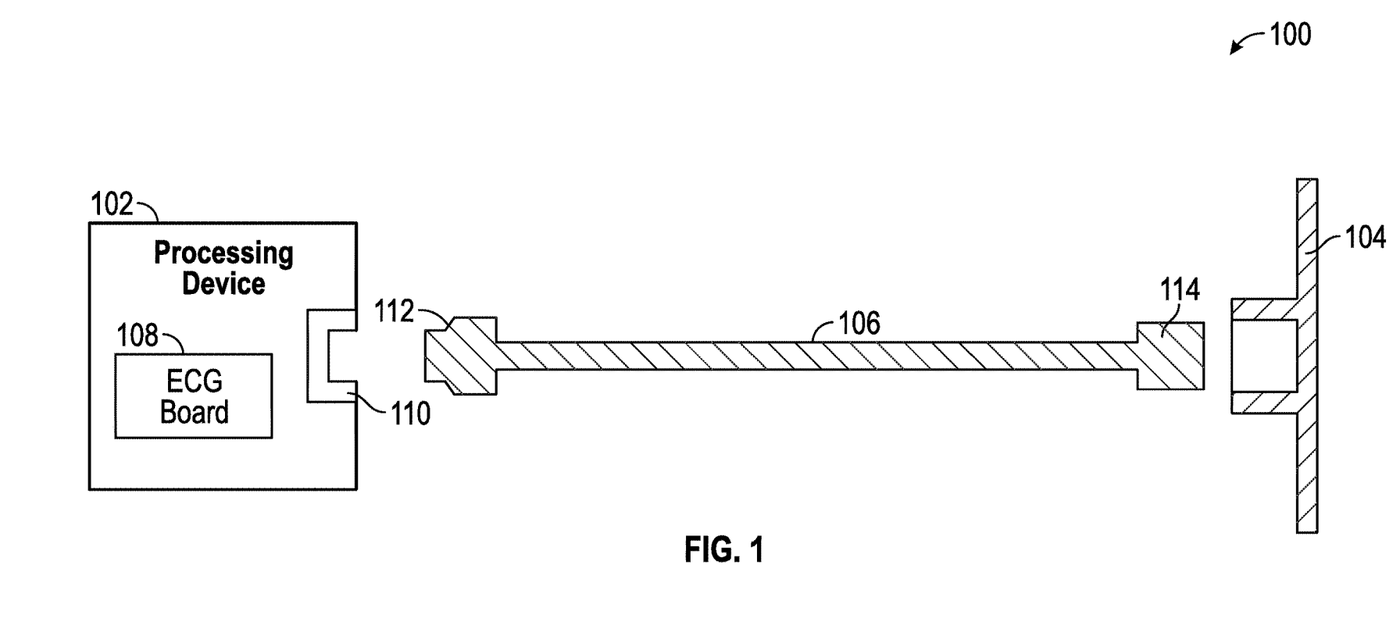
FIG. 1 is a schematic diagram illustrating the components of an electrocardiography system in accordance with various embodiments.

FIG. 1 schematically illustrates an electrocardiography system 100 in accordance with various embodiments. The system 100 includes a processing device 102, one or more (typically multiple) electrodes 104, and a cable 106 (herein also "patient cable") connecting the electrode(s) 104 to the processing device 102. The electrode(s) 104 may each be packaged with an associated backing and skin patch into an "electrode assembly" (see FIGS. 4A and 4B); the electrode assemblies be designed to have industry "best in class" skin-to-electrode contact properties, including adhesion properties, low impedance, and lack of noise injection from movement of the cable and/or patient. The processing device 102 may be, e.g., a desktop, laptop, or tablet computer, and may include a processing board 108 (labeled "ECG board"), implemented in analog and/or digital electronics, for processing the incoming electrocardiogram signals. In accordance with various embodiments, the processing board 108 provides advanced signal-processing functionality whose performance potential is fully realized only if the incoming raw signals acquired by the electrodes 104 meet certain minimum signal-quality requirements (e.g., noise levels below those usually present in electrocardiogram signals acquired with conventional electrodes). Such advanced signal-processing functionality may, for example (and without limitation), involve transforming the measured time-domain signals into frequency-domain or time-frequency-domain signals (e.g., using Fourier transform or wavelet transform), and identifying features in those domains that would not be present or not as easily ascertainable in the time domain and/or defining new quantitative parameters that may correlate with disease conditions. Non-limiting examples of the advanced signal-processing functionality contemplated herein are described in U.S. patent application Ser. No. 15/271,155, filed on Sep. 20, 2016 and entitled "Quantitative Heart Testing," which is hereby incorporated herein by reference.

The processing device 102 and patient cable 106 interface via a cable connector 110 included in the processing device 102 and a mating device connector 112 on one end of the cable 106; in some embodiments, the connectors 110, 112 are custom DB15 connectors (e.g., as described with reference to FIG. 2B below). On the other end of the patient cable 106, one or more electrode connectors 114 provide a mechanical and electrical connection to the one or more respective electrodes 104. While only one electrode 104 and only corresponding electrode connector 114 are shown, it is to be understood that, in many embodiments, the cable fans out into multiple cable ends, each having its own electrode connector 114 configured to mate with a separate respective electrode 104. For example, in many medical applications, ten electrodes are placed on a patient to acquire a 12-lead electrocardiogram; these ten electrodes can be connected to the same processing device via a cable that includes ten wires terminating in ten respective electrode connectors 114.

In accordance with various embodiments, the electrode connectors 114 on the patient cable 106 are mechanically keyed to the electrodes 104 so as to prevent the cable 106 to be connectable to standard conventional electrodes (which may provide signals of insufficient signal quality to take full advantage of advanced signal processing functionality). Similarly, the connectors 110, 112 of the interface between the processing device 102 and the patient cable 106 may deviate in their configuration from standard connectors so as to mechanically and/or electronically key the processing device 102 to the patient cable 106 and prevent other (e.g., standard conventional) cables to work with the processing device 102. Using mechanical and/or electronical keying on both ends of the cable, it can be ensured that only desired electrodes 104 are connectable to the processing device 102. Example embodiments of such keying will now be described in detail.

Figure 2A:
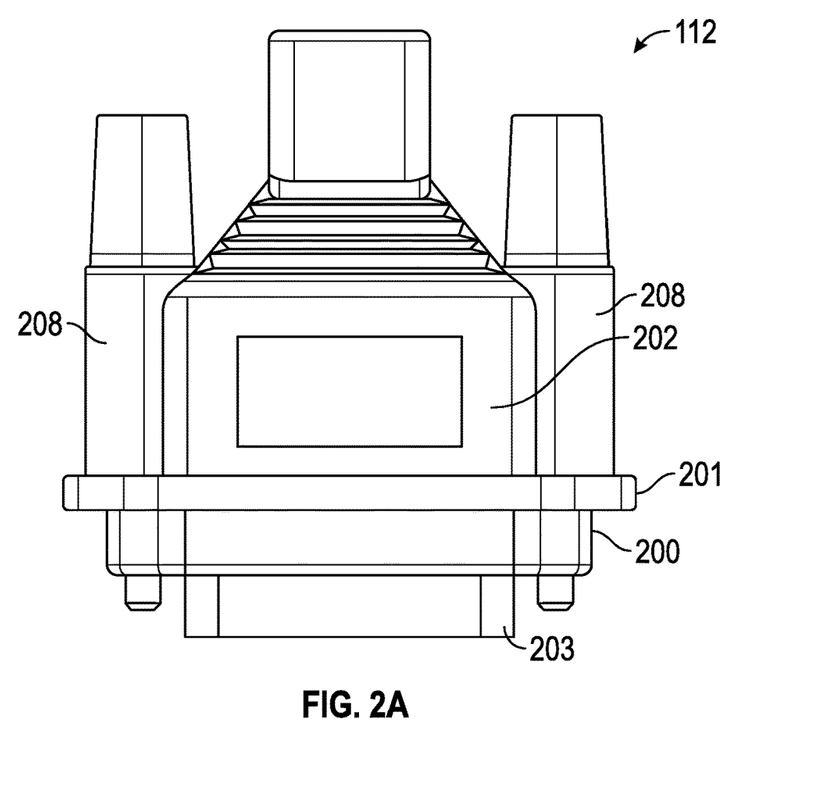
FIG. 2A is a side view of an example device connector of a cable in accordance with various embodiments.
Figure 2B:
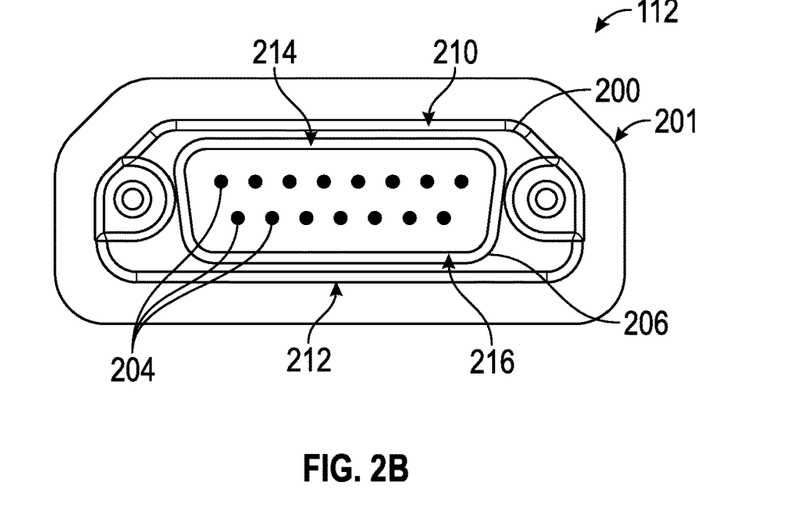
FIG. 2B is a bottom view of a device connector of a cable in accordance with an example embodiment.
Figure 3A:
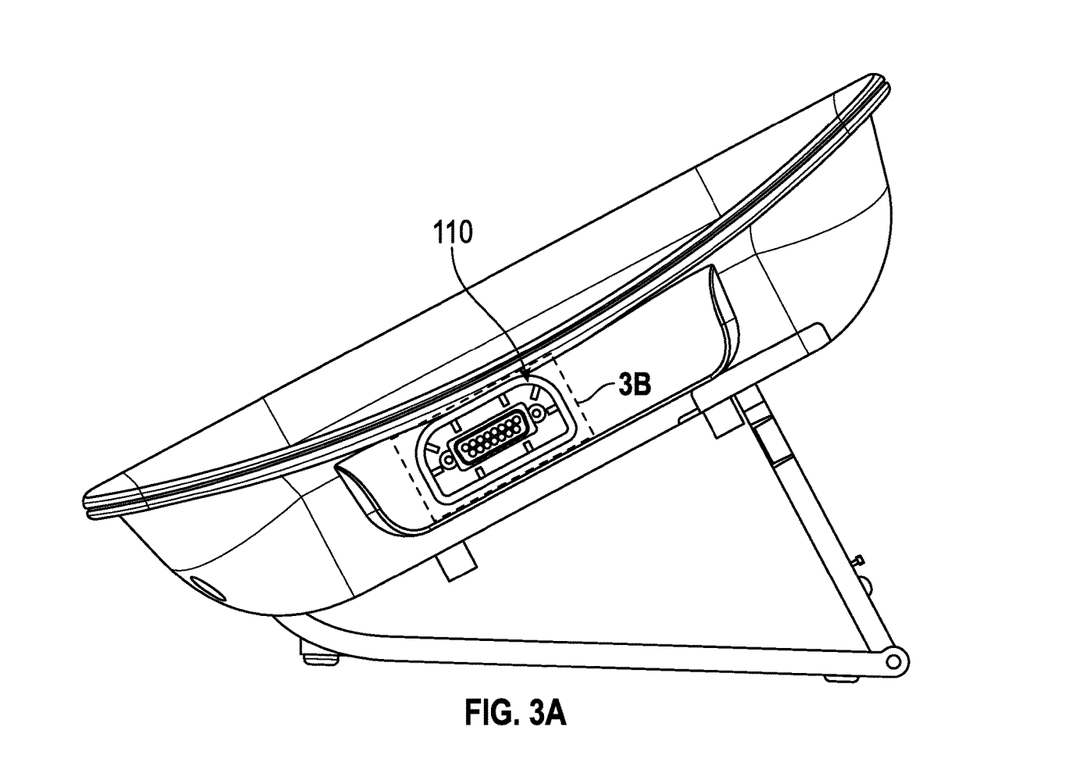
FIG. 3A is a side view of a processing device with a cable connector that mates with the device connector of FIG. 2B, in accordance with an example embodiment.

FIGS. 2A and 2B illustrate, in side and bottom views, respectively, an example device connector 112 of a cable 106 in accordance with various embodiments. FIG. 3A shows, in side view, an example processing device 102 with a cable connector 110 that mates with the device connector 112 of FIGS. 2A and 2B; an enlarged side view of the cable connector 110 itself is provided in FIG. 3B. The device connector 112 includes a plug 200 protruding from a plug stop 201 on a cable backshell 202. The plug 200, plug stop 201, and backshell 202 may form an integral structure made, e.g., of plastic. The plug 200 may be sized and shaped for insertion into a corresponding jack 300 of the cable connector 110 within the processing device 102. For example, the jack 300 may include a plurality of pegs 301 extending inward from an interior surface of the jack 300, with lengths, positions, and orientations of the pegs 301 such that the plug 200 can be inserted into the center region of the jack 300 surrounded by the pegs 301 while the plug stop 201 comes to rests against the pegs 301, blocking further advancement of the device connector 112.

The device connector 112 further includes, protruding from the plug 200, a contact block 203 including a number of contacts 204 surrounded by a shroud (or "guide") 206 (e.g., made of metal). In the example shown, a total of fifteen contacts 204 are arranged in two rows of seven and eight contacts, respectively, as is standard in DB15 connectors. As shown, the device connector 112 may be a male connector with pin contacts 204 (indicated by the filled circles in FIG. 2B) that are to be received within respective socket contacts 302 (indicated by hollow circles in FIGS. 3A and 3B) of a female cable connector 110 in the processing device 102. Alternatively, the device connector 112 may be a female connector with socket contacts to receive respective pin contacts of a male cable connector 110 in the processing device 102. Either way, the contacts 302 of the cable connector 110 in the processing device 102, like those of the device connector 112 of the cable 106, are surrounded by a shroud 304, which is sized and shaped to mate with the shroud 206 of the device connector 112. The shroud of the female connector 112 (whether this be the device connector 112 or the cable connector 110) is generally sized to just fit within the shroud of the male connector. The device connector 112 may further include jackscrews 208 to be screwed into corresponding threaded sockets 306 in the jack 300 of the cable connector 110 to securely connect the cable 106 to the processing device 102.

Figure 3B:
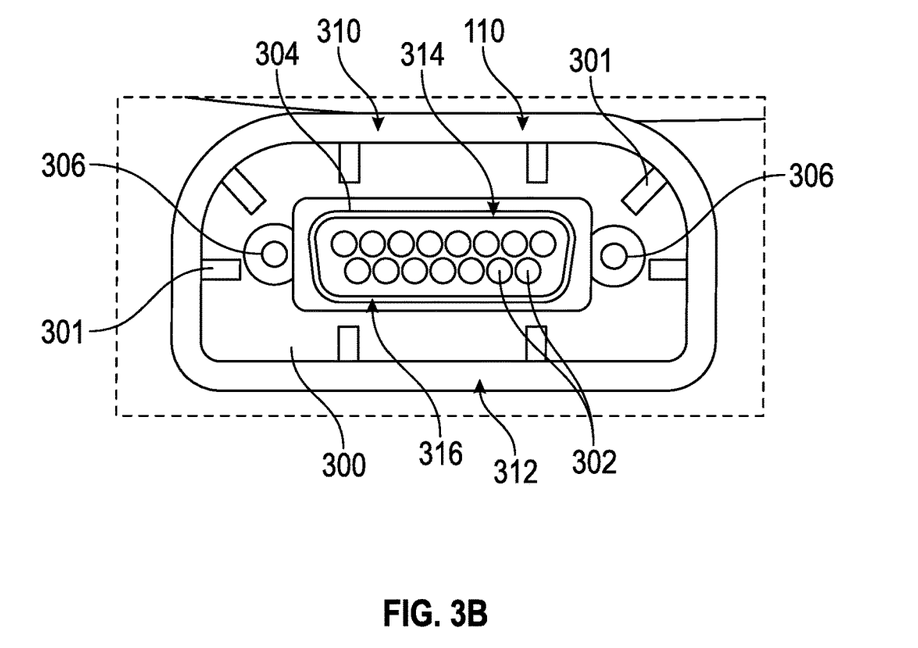
FIG. 3B is an enlarged side view of the cable connector of FIG. 3A.

The plug 200 may be characterized by an asymmetric shape configured to dictate the orientation with which the plug 200 is plugged into the space defined by the pegs 301 of the jack 300. For example, as shown, the plug 200 may have, in a direction parallel to the rows of contacts, two edges 210, 212 of different lengths. The shorter edge 210 can be thought of as resulting from removal of two corners from the otherwise substantially rectangular (e.g., rectangular but for rounded corners) plug 200. (In the illustrated example, the plug stop 201 has a similar shape, mating with the shape of the jack 300. In general, however, the shape of the plug stop 201 and jack 300 are independent from the shape of the plug 200. For example, the plug stop 201 and jack 300 may be simply rectangular.) The pegs 301 in the jack 300 are configured to allow for insertion of the plug 200 in only one direction. For instance, the jack 300 may include, at a top edge 310 thereof (which, in the illustrated example, is the shorter edge), pegs 301 in the corners that prevent the long edge 212 of the plug 200 from fitting; the bottom edge 312 of the jack 300, however, does not include such pegs in the corners. Accordingly, the plug 200 can only be received within the jack 300 if its shorter and longer edges 210, 212 are aligned with the top and bottom edges 310, 312, respectively, of the jack 300.

The relative orientation of the device connector 112 and cable connector 110 (when connected) is also fixed by the shape of the shrouds 206, 304. As shown, the shrouds 206, 304 may be trapezoid, each including shorter and longer edges in a direction parallel to the rows of contacts; the shorter edge may be placed adjacent to the row of seven contacts and the longer edge adjacent to the row of eight contacts. In accordance with various embodiments, the longer edge 214 of the shroud 206 of the device connector 112 is adjacent to (or, put differently, closer to) the shorter edge 210 of the plug 200, and the shorter edge 216 of the shroud 206 of the device connector 112 is adjacent (or closer) to the longer edge 212 of the plug 200. Accordingly (to ensure consistency with the plug-in orientation dictated by the plug shape and peg configuration in the jack 300), the longer edge 314 of the shroud 304 of the cable connector 110 is adjacent (or closer) to the top (as shown, the shorter) edge 310 of the jack 300, and the shorter edge 316 of the shroud 304 of the cable connector 110 is adjacent (or closer) to the bottom (as shown, the longer) edge 312 of the jack 300.

Figure 2C:
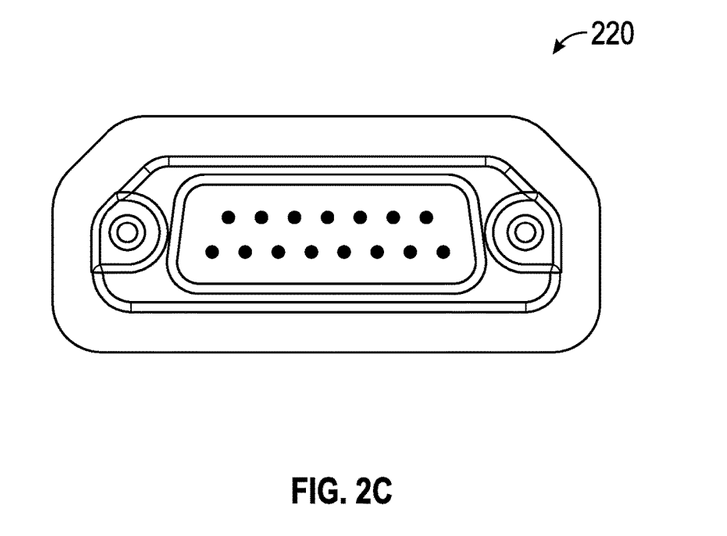
FIG. 2C is a bottom view of a conventional connector.

Importantly for the purpose of keying the cable 106 to the processing device 102, the connector configuration illustrated in FIGS. 2B and 3B is different from that used in conventional connectors. A conventional device connector 220 is shown, for comparison, in FIG. 2C (in a bottom view). In the conventional connector 220, the shorter edge of the shroud is adjacent (or closer) to the shorter edge of the plug, and the longer edge of the shroud is adjacent (or closer) to the longer edge of the plug—that is, the orientation of the shroud relative the plug is the inverse of that used in the device connector 112 of the embodiment depicted in FIG. 2B. As a result, the device connector 220 of a conventional cable cannot be plugged into the jack 300 of the cable connector 110 included in the processing device 102. In other words, the orientation inversion of the shroud (as compared to a conventional connector) in accordance with various embodiments, which is applied to both the device connector 112 of the cable 106 and in an analogous manner to the cable connector 110 of the processing device, ensures that only a patient cable 106 with the above-described custom device connector 112 (and not a cable with a standard conventional connector 220) can connect to the processing device 102.

In addition to the mechanical keying between the processing device 102 and the patient cable 106, various embodiments use non-standard pin assignments for electronic keying. Thus, even if the mechanical safeguards are circumvented, e.g., by physical manipulation of the plug of a conventional connector 220 to fit into the jack 300 of the custom cable connector 110, the conventional cable would still not work with the processing device 102.

Figure 4A:
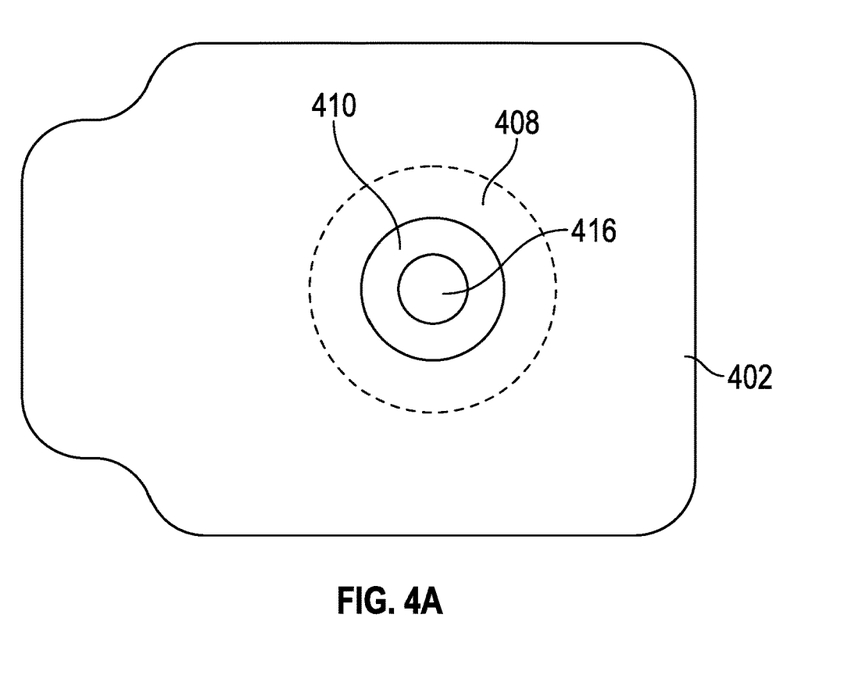
FIGS. 4A and 4B are bottom and side views, respectively, of an example electrode assembly in accordance with various embodiments.
Figure 4B:
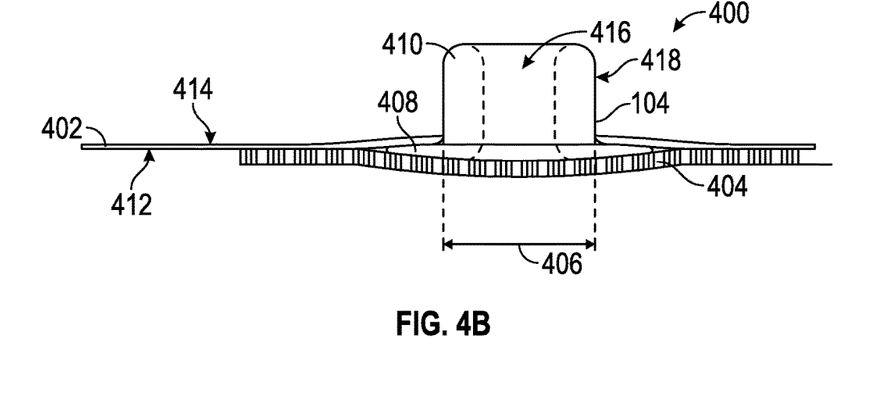

Turning now to the interface between the patient cable 106 and the electrodes 104, FIGS. 4A and 4B illustrate an example electrode assembly 400 in accordance with an embodiment in bottom and side views, respectively. The electrode assembly 400 includes an electrically conductive electrode 104 (e.g., made of a metal or plastic anodized with a conductor metal such as silver oxide)), an adhesive-tape backing 402, and an electrically conductive (and usually self-adhesive) skin patch 404 (e.g., a hydrogel patch) placed in contact with the electrode 104. The skin patch 404 is, in use, placed against the patient's skin, and serves to provide proper skin-to-electrode electrical contact. The backing 402 has an (e.g., circular) opening 406, through which the electrode 104 extends. The electrode 104 includes a ring-shaped disk portion 408 and, perpendicularly extending from the ring-shaped disk portion 408 at an inner diameter thereof, a hollow-post portion 410 (e.g., such that the inner diameter of the ring-shaped disk portion 408 coincides with the inner diameter of the hollow-post portion 410 at a bottom end thereof). The ring-shaped disk portion 408 is placed on the bottom side 412 of the backing 402, between the backing 402 and the skin patch 404. The hollow-post portion 410 protrudes from the other (top) side 414 of the backing 402, and is aligned with the opening 406 of the backing 402.

The hollow-post portion 410 defines a bore 416 through the electrode 104, which is shaped and sized to receive a mating post on the electrode connector 114. As shown, the bore 416 may be centered within the hollow-post portion 410, and both the bore 416 (which defines the inner surface of the hollow-post portion 410) and the exterior surface 418 of the hollow-post portion 410 may be cylindrical in shape. It is also possible, however, that the wall thickness of the hollow-post portion 410 varies along the length of the hollow-post portion 410 such that, e.g., the exterior surface 418 deviates from cylindrical shape (i.e., has a variable diameter along the length). Further, in some embodiments, the bore 416 may deviate from perfect cylindrical shape, allowing, for example, for an annular lip extending from the inner surface of the hollow-post portion 410 to provide a snap fit between the hollow-post portion 410 and the mating post of the electrode connector 114 on the patient cable 106 (as explained further below).

Figure 5A:
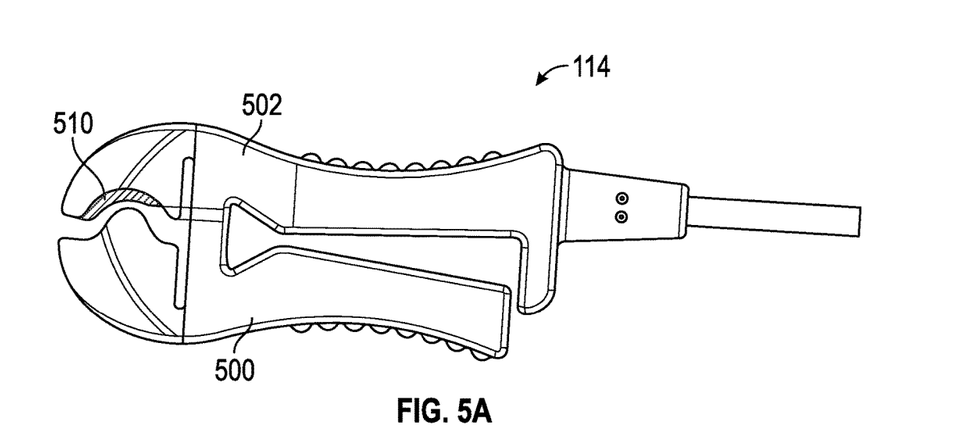
FIGS. 5A, 5B, and 5C are top, side, and perspective views, respectively, of an example electrode connector of a cable in accordance with various embodiments.
Figure 5B:
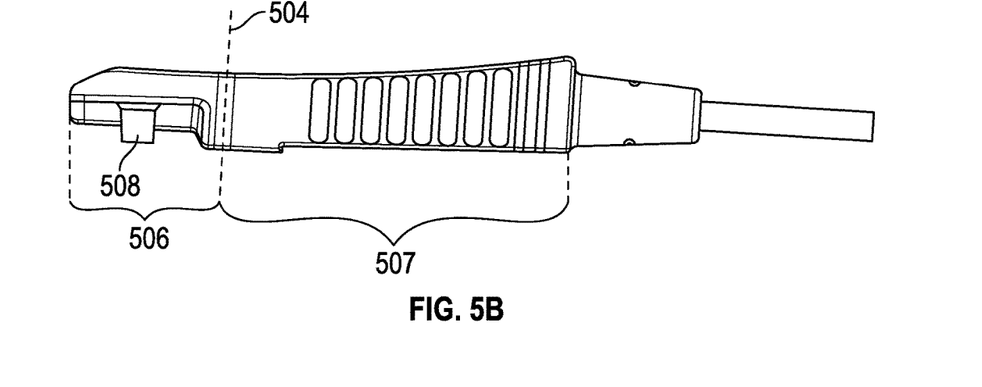
Figure 5C:
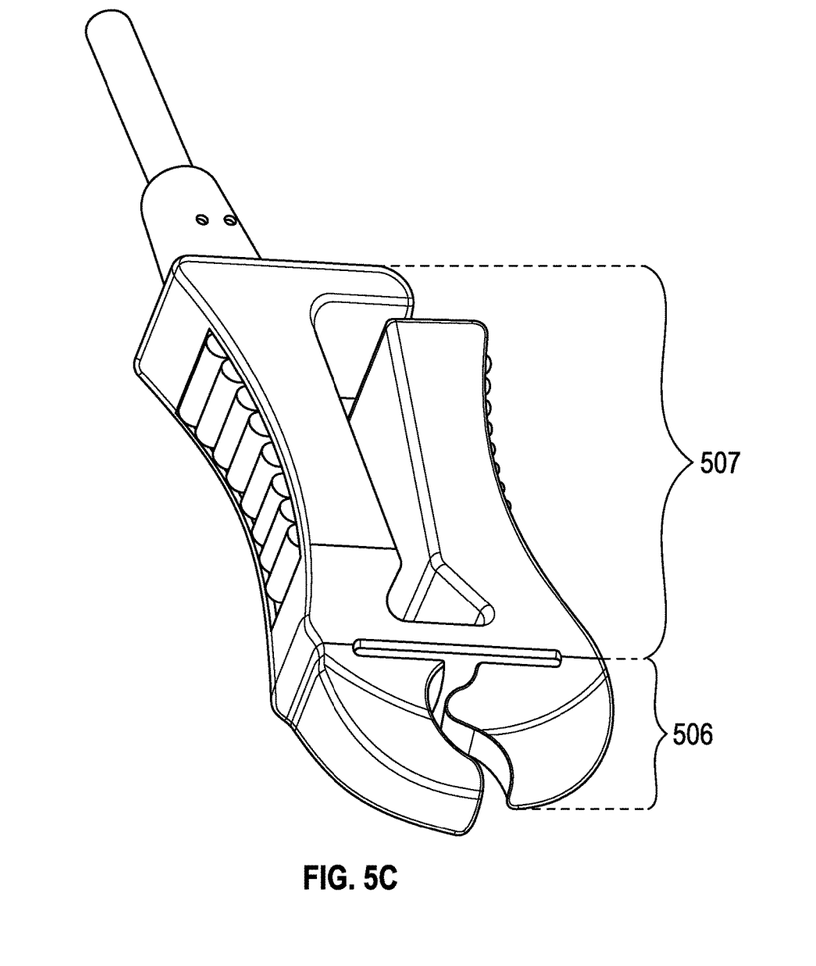

FIGS. 5A, 5B, and 5C are top, side, and perspective views, respectively, of an example electrode connector 114 designed to connect to the electrode 104 (more specifically, the hollow-post portion 410 of the electrode 104) depicted in FIGS. 4A and 4B, in accordance with various embodiments. The electrode connector 114 includes two clamp arms 500, 502 connected to each other at least at an axis 504 and movable relative to each other about (and in a plane perpendicular to) the axis 504 (which is herein also referred to as the "axis of rotation"). For example, in some embodiments, the two clamp arms 500, 502 form an integral contiguous structure made in large part of a flexible material (e.g., a medical-grade plastic) that allows the arms 500, 502 to bend such that the angle they enclose (measured from a vertex located at the axis 504) can vary at both the "clamp end" 506 (generally the distal end, i.e., the end situated away from the connection to the cable) and the "grabber end" 507 (generally the proximal end) of the clamp arms 500, 502. In other embodiments, the clamp arms are rigid and rotatably connected to each other via hinge mechanism along the axis 504 (which thereby forms the axis of rotation). Regardless of the implementation details, the electrode connector 114 is configured to open at the clamp end 506 upon application of inward pressure to the grabber end 507 of the arms 500, 502, and to close at the clamp end 506 upon release of such pressure (e.g., due to restoring forces that are intrinsic to the clamp arms in flexible structures, or are deliberately introduced in rigid structures by a mechanical bias mechanism such as, for instance, spring loading).

The clamp arms 500, 502 are configured to engage with the electrode 104 (more specifically, the hollow-post portion 410 of the electrode 104) at clamp end 506, where one of the clamp arms (500) includes a post 508 extending therefrom in a direction parallel to the axis of rotation 504 (e.g., in FIG. 5A, out of the plane of the drawing). The post 508 is shaped and sized to fit within the bore 416 of the hollow-post portion 410 of the electrode 104. The other clamp arm 502 is, at an inner surface of the clamp end 506, complementary in shape to a portion of the exterior surface 418 of the hollow-post portion 410 of the electrode 104, and includes, at the inner surface at a position opposite to the post, an electrically conductive contact surface 510 (e.g., in the form of a metallic layer disposed on the otherwise largely plastic clamp arm 500). When pressed against the exterior surface 418 of the hollow-post portion 410, the contact surface 510 establishes an electrical contact with the hollow-post portion 410 of the electrode 104. An electrical conductor (not shown) embedded within the electrode connector 114 electrically connects the contact surface 510 to a wire running within the patient cable 106. The connector 114 can be connected to the electrode 104 by pressing the clamp arms 500, 502 at the grabber end 507 (e.g., between index finger and thumb) to open the clamp end 506, placing the post 508 of the first clamp arm 500 into the bore 416 of the hollow-post portion 410 of the electrode 104, and then releasing the clamp arms 500, 502 such that the hollow-post portion 410 of the electrode 104 becomes clamped between the post 508 of the first clamp arm 500 and the second clamp arm 502 and the contact surface 510 is brought in secure contact with the exterior surface 418 of the hollow-post portion 410 of the electrode 104. While the described clamp mechanisms by itself may suffice to securely attach the electrode connector 114 of the cable 106 to the electrode 104, an optional snap mechanism may be employed, in accordance with some embodiments, to further increase the reliability of the attachment: in this case, the post 508 on the clamp arm 500 may feature an annular groove and the bore 416 of the hollow-post portion 410 a mating annular lip such that the post 508 snaps into the bore 416.

As will be readily appreciated by a person of ordinary skill in the art given the benefit of the present disclosure, the connector embodiments described herein achieve the intended mechanical keying between the processing device and patient cable and between the patient cable and electrode(s) of an electrocardiography system in accordance herewith. Various modifications to the depicted embodiments that still accomplish the mechanical keying in the same or a similar manner as described herein are possible and intended to be within the scope of the disclosed subject matter.

What is claimed is:

1. An electric cable comprising: one or more electrode connectors at a first end of the electric cable, at least one of the one or more electrode connectors comprising:

first and second clamp arms connected at an axis of rotation and movable relative to each other about the axis of rotation, wherein the first and second clamp arms comprise respective inner surfaces facing one another and respective top and bottom surfaces, wherein the first clamp arm comprises a post protruding from the bottom surface of the first clamp arm, a longitudinal axis of the post extending parallel to and spaced apart from the axis of rotation; and wherein the inner surface of the second clamp arm comprises an electrically conductive contact surface that is electrically connected to a wire running within the cable.

2. The electric cable of claim 1, wherein the first and second clamp arms are configured to engage with a hollow-post electrode.

3. The electric cable of claim 2, wherein the post is configured to fit within a bore of the hollow-post electrode.

4. The electric cable of claim 2, wherein the inner surface of the second clamp arm is configured to complement a shape of a portion of an exterior surface of the hollow-post electrode.

5. The electric cable of claim 1, wherein a portion of the first and second clamp arms is made of a flexible medical-grade plastic.

6. The electric cable of claim 1, wherein the first and second clamp arms are configured to open at a clamp end thereof upon application of pressure onto a grabber end of the first and second clamp arms and are configured to close at the clamp end upon release of the pressure onto the grabber end of the first and second clamp arms.

7. The electric cable of claim 1, further comprising a device connector at a second end of the electric cable.

8. The electric cable of claim 7, wherein the device connector comprises a plug having a pair of parallel edges of different lengths and, protruding from the plug, a plurality of contacts enclosed by a trapezoid shroud with a pair of parallel edges, a shorter one of the pair of parallel edges of the trapezoid shroud being adjacent to a longer one of the pair of parallel edges of the plug and a longer one of the pair of parallel edges of the trapezoid shroud being adjacent to a shorter one of the pair of parallel edges of the plug.

9. The electric cable of claim 7, wherein the device connector is configured to at least one of mechanically or electrically mate with a mating cable connector of a processing device.

10. A method for connecting a hollow-post electrode to a processing device, the method comprising:
    using a cable comprising an electrode connector at a distal end, wherein the electrode connector comprises first and second clamp arms, and a device-connector at a proximal end, wherein the first and second clamp arms are connected at an axis of rotation and movable relative to each other about the axis of rotation, and wherein the first and second clamp arms comprise respective inner surfaces facing one another and respective top and bottom surfaces:
    connecting the electrode connector to the hollow-post electrode by opening the clamp arms by applying pressure onto grabber ends of the first and second clamp arms and inserting a post extending from the bottom surface of the first clamp arm into a mating bore in the hollow-post electrode, wherein the post has a longitudinal axis parallel to and spaced apart from the axis of rotation;
    closing the first and second clamp arms by releasing the pressure on the grabber ends to bring an electrically conductive contact surface at the inner surface of the second clamp arm into contact with an exterior surface of the hollow-post electrode; and
    inserting the device-connector into a mating cable connector within the processing device.

* * * * *

UNITED STATES PATENT AND TRADEMARK OFFICE
CERTIFICATE OF CORRECTION

PATENT NO. : 10,170,846 B2
APPLICATION NO. : 15/454821
DATED : January 1, 2019
INVENTOR(S) : Hilz et al.

Page 1 of 1

It is certified that error appears in the above-identified patent and that said Letters Patent is hereby corrected as shown below:

In the Claims

In Column 9, Line 10, in Claim 6, after "onto", delete "a"

In Column 9, Line 10, in Claim 6, delete "end" and insert --ends-- therefor

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*